Figure 1:
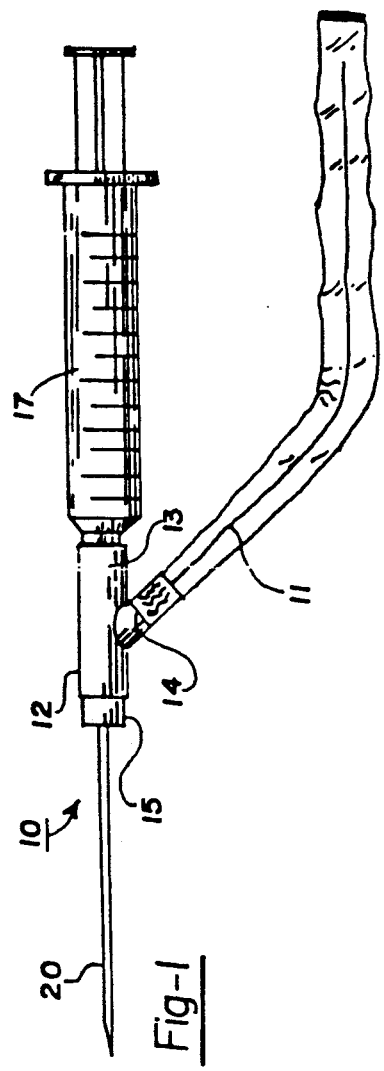

United States Patent [19]

Vaillancourt

[11] Patent Number: 5,290,242

[45] Date of Patent: Mar. 1, 1994

[54] BLOOD VESSEL Y-SITE CONNECTOR

[76] Inventor: Vincent L. Vaillancourt, 14 Bunyan Dr., Livingston, N.J. 07039

[21] Appl. No.: 960,729

[22] Filed: Oct. 14, 1992

[51] Int. Cl.$^5$ .............................................. A61M 5/32
[52] U.S. Cl. ..................................... 604/163; 604/284; 604/171
[58] Field of Search ............... 604/163, 167, 169, 171, 604/284, 164

[56] References Cited

U.S. PATENT DOCUMENTS

| | | | |
|---|---|---|---|
| 3,055,361 | 9/1962 | Ballard | 604/163 |
| 3,585,996 | 6/1971 | Reynolds | 604/158 |
| 3,739,778 | 6/1973 | Monestere | 604/167 |
| 3,786,810 | 1/1974 | Pannier et al. | 604/158 |
| 4,235,234 | 11/1980 | Spaven et al. | 604/171 |
| 4,525,157 | 6/1985 | Vaillancourt | 604/165 |
| 4,569,347 | 2/1986 | Frisbie | 604/171 |
| 4,652,256 | 3/1987 | Vaillancourt | 604/168 |
| 4,655,750 | 4/1987 | Vaillancourt | 604/165 |
| 4,813,938 | 3/1989 | Raulerson | 604/167 |
| 4,842,591 | 6/1989 | Luther | 604/167 |
| 4,935,010 | 6/1990 | Cox et al. | 604/167 |
| 4,960,412 | 10/1990 | Fink | 604/167 |
| 5,041,097 | 8/1991 | Johnson | 604/167 |
| 5,062,836 | 11/1991 | Wendell | 604/167 |
| 5,147,314 | 9/1992 | Vaillancourt | 604/171 |

FOREIGN PATENT DOCUMENTS

| | | | |
|---|---|---|---|
| 56103 | 6/1982 | European Pat. Off. | 604/164 |
| 1534119 | 7/1968 | France | 604/163 |

Primary Examiner—John G. Weiss
Attorney, Agent, or Firm—Francis C. Hand

[57] ABSTRACT

A collapsible sheath secured in seal-tight manner on an arm of a Y-site connector to define a closed chamber for a guide wire. The guide wire is mounted at one end in a seal ring located in a bore of the arm of the connector and can be slid through the ring to be implanted in a body cavity, such as a blood vessel.

6 Claims, 1 Drawing Sheet

BLOOD VESSEL Y-SITE CONNECTOR

This invention relates to an arterial Y-site connector. More particularly, this invention relates to a blood vessel connector assembly for introducing a guide wire into a body cavity.

As is known, various techniques have been used for the introduction of a catheter or a guide wire into a body cavity, such as a vein, artery and the like. For example, U.S. Pat. No. 4,813,938 describes the use of a syringe for the introduction of a catheter or guide wire into a blood vessel. Other types of devices for the introduction of a catheter into a blood vessel have also been described in U.S. Pat. No. 4,235,232. However, in these previously known devices, a catheter or guide wire can be exposed to the environment before or during placement. Accordingly, when the guide wire and/or catheter enters the body cavity, any potential contamination is immediately transported into the patient.

Accordingly, it is an object of the invention to be able to place a guide wire in a body cavity under closed system conditions.

It is another object of the invention to reduce the risk of contamination of a patient during the introduction of a guide wire.

Briefly, the invention provides an arterial Y-site connector assembly which comprises a Y-site connector of generally known construction having a first arm defining a first passage, a second arm having a second passage and a third arm connected with the first two arms as well as a needle mounted in and extending from the third arm while being in communication with the passages in the first two arms.

In accordance with the invention, a flexible sheath is fixed to and extends from the second arm in seal-tight relation to define a closed chamber and a guide wire is slidably mounted at one end in the passage of the second arm and extends within the closed chamber of the sheath. The construction of the connector assembly is such that the guide wire is maintained in a closed manner at all times.

The connector may be constructed in a similar fashion to the Y-site connector as described in U.S. Pat. No. 5,147,314. Further, any suitable cover may be mounted over the needle extending form the connector in order to maintain the needle under sterile conditions. Likewise, a syringe may be mounted in the first arm of the connector on a closed relationship or the connector and syringe may be constructed as to permit insertion of the syringe into the connector in a closed system manner.

Figure 2:
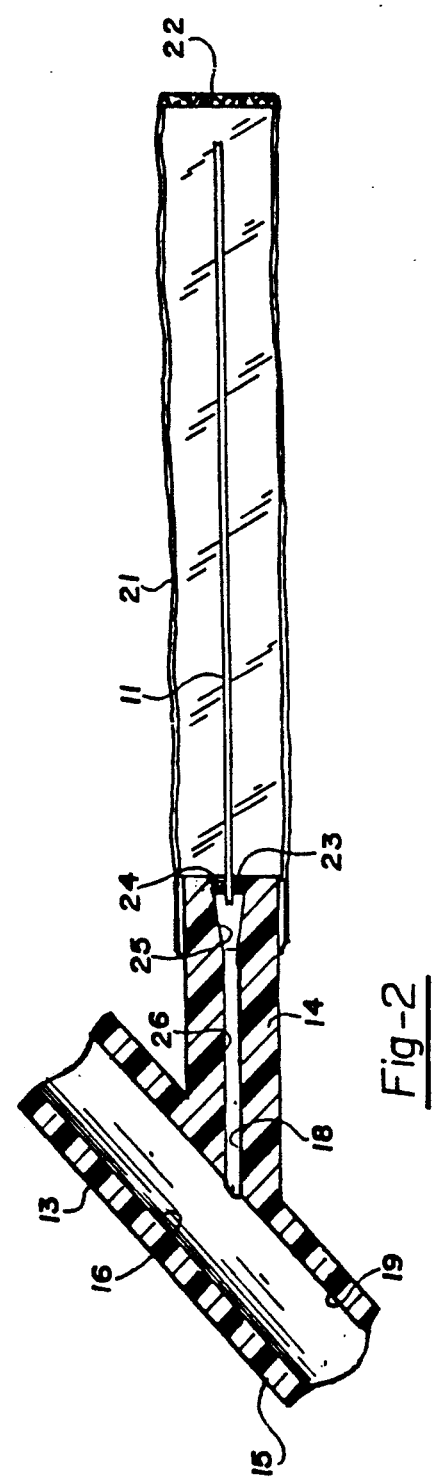

These and other objects of the invention will become more apparent from the following detailed description taken in conjunction with the accompany drawings wherein:

FIG. 1 illustrates a view of a blood vessel Y-site connector assembly constructed in accordance with the invention; and FIG. 2 illustrates a part cross sectional view of the connector of the connector assembly in accordance with the invention.

Referring to FIG. 1, the connector assembly 10 is constructed as a blood vessel Y-site connector assembly for the introduction of a guide wire 11 into an artery or other suitable body cavity. In addition, the connector assembly 10 is constructed to permit a fluid to be injected into the artery.

As shown, the blood vessel Y-site connector assembly 10 includes a Y-site connector 12 having three arms or branches 13, 14, 15. One arm 13 is provided with a passage 16 (see FIG. 2) for receiving a syringe 17. A second arm 14 is provided with a passage or bore 18 which receives the wire 11 and which is of smaller diameter than the passage 16 and connects with the passage 16 in angular relation. The third arm 15 is connected to the first two arms 13, 14 and contains a passage 19 which is coaxial and co-extensive of the first passage 16 while communicating with both passages 16, 18 to conduct fluid therethrough as well as to receive the wire 11 as described below.

In addition, the connector assembly 10 has a hollow needle 20 mounted in and extending coaxially from the passage 19 in the third arm 15.

Referring to FIG. 2, a flexible sheath 21 is fixed to and extends from the second arm 14 of the connector 12 in seal-tight relation to define a closed chamber containing the wire 11 in sealed relation. As indicated, the sheath 21 is of flexible nature and has one end secured to the connector arm 14 in seal-tight relation. In addition, a closure 22 is disposed at a proximal end of the sheath 21 to seal off the interior of the sheath 21. The closure 22 may be in the form of a rigid member suitably secured within the sheath 21. Alternatively, the sheath 21 may have a collapsed proximal end which is sealed on itself.

As shown in FIG. 2, the guide wire 11 is slidably mounted at one end in the bore 18 of the second arm 14 and extends within the closed chamber of the sheath 21. In this respect, a means in the form of a seal ring 23 is disposed in the entrance end of the bore 18 of the arm 14 in seal-tight relation to slidably receive the guide wire 11 therein. To this end, the bore 18 has a mouth 24 of enlarged diameter to receive the seal ring 23 and a conical portion 25 connecting the mouth 24 to a reduced diameter portion 26 leading to the passage 16 within the first arm 13 of the connector 12. The reduced diameter portion 26 of the bore 18 in the arm 14 has a diameter of a size to slidably receive the guide wire 11 therein.

The connector assembly 10 can be packaged in a sterile package (not shown). In addition, a suitable cover (not shown) can be disposed over the needle 20 and secured on the connector 12 so as to retain the needle 20 in a sterile condition.

When the connector assembly 10 is put into use, the needle 20 is passed into a blood vessel, for example, an artery of a patient. Thereafter, by manually collapsing the sheath 21 so as to permit digital (manual) engagement of the guide wire 11 between two fingers, the guide wire 11 can be slid forwardly through the seal ring 23 and the bore 18 in the arm 14 of the connector 12 into the coaxially aligned passages 16, 19 and, thence, through the needle 20 into the artery of the patient. During this time, the guide wire 11 is maintained in a sealed condition, i.e. in a closed system.

Before or after placement of the guide wire 11, the syringe 17 can be activated so as to inject fluids into the blood vessel.

The guide wire 11 can be left in place while the remainder of the connector assembly 10 is withdrawn from the patient.

The connector 12 may be constructed so as to permanently receive a hollow tip of the syringe 17. Further, the syringe 17 can be used to aspirate fluid and aid in determining that a vessel has been penetrated. For Example, after a flashback of blood or other body fluid into the syringe 17, the guide wire 11 can be threaded through the connector 12 into the blood vessel while remaining under a closed system.

Any suitable means may be used for securing the flexible sheath 21 to the arm 14 of the connector 12, for example, adhesives may be used. Further, the connector 12 may be made of any suitable materials, such as plastic, while the sheath 21 is made of any suitable flexible material which can be readily collapsed so as to permit manual grasping of the guide wire 11 for pushing forwardly through the connector 12.

The invention thus provides a connector assembly which permits the storage of a guide wire in a sterile manner while also permitting the introduction of the guide wire into a body cavity, such as a blood vessel, in a sterile manner.

What is claimed is:

1. A blood vessel Y-site connector assembly comprising
   a Y-site connector having a first arm having a first passage, a second arm having a second passage, a third arm connected with said first and second arms and having a third passage communicating with said first and second passages, and a hollow needle mounted in and extending from said third arm, said needle being in communication with said third passage,
   a flexible sheath fixed to and extending from said second arm in seal-tight relation to define a closed chamber; and
   a guide wire slidably mounted at one end in said second passage of said second arm and extending within said closed chamber of said sheath.

2. An assembly as set forth in claim 1 which further comprises a seal ring in said second passage disposed in seal-tight relation to said second arm and slidably receiving said guide wire therein.

3. An assembly as set forth in claim 2 which further comprises a closure at an end of said sheath remote from said second arm to close said chamber thereat.

4. An assembly as set forth in claim 2 wherein said second passage in said second arm is a bore having a mouth receiving said seal ring therein, a reduced diameter portion leading to said first passage and conical portion connecting said mouth to said reduced diameter portion and said reduced diameter has a diameter of a size to slidably receive said guide wire therein.

5. A assembly as set forth in claim 4 wherein said first passage in said first arm is coaxial of a third passage in said third arm, said third passage being of a diameter greater than said diameter of said second passage.

6. An assembly as set forth in claim 5 wherein said second passage is disposed angularly of said first and third passages.

* * * * *

UNITED STATES PATENT AND TRADEMARK OFFICE
CERTIFICATE OF CORRECTION

PATENT NO. : 5,290,242
DATED : March 1, 1994
INVENTOR(S) : Vaillancourt

It is certified that error appears in the above-identified patent and that said Letters Patent is hereby corrected as shown below:

Column 4, line 17 after "and" insert -a-

Signed and Sealed this

Twenty-eighth Day of June, 1994

Attest:

BRUCE LEHMAN

Attesting Officer      Commissioner of Patents and Trademarks